United States Patent [19]

Jones et al.

[11] Patent Number: 5,209,459
[45] Date of Patent: May 11, 1993

[54] CHEMICAL PROCESS

[75] Inventors: Raymond V. H. Jones, West Lothian, Scotland; John M. Bloomer, Farncome, England

[73] Assignee: Imperial Chemical Industries PLC, Millbank, United Kingdom

[21] Appl. No.: 906,248

[22] Filed: Jun. 29, 1992

[30] Foreign Application Priority Data

Jul. 16, 1991 [GB] United Kingdom ............... 9115246

[51] Int. Cl.$^5$ ............................................. C07F 3/02
[52] U.S. Cl. ............................................. 260/665 G
[58] Field of Search ............................. 260/665 G

[56] References Cited

U.S. PATENT DOCUMENTS

| | | | |
|---|---|---|---|
| 2,056,822 | 10/1936 | Britton et al. | 260/665 G |
| 2,552,676 | 5/1951 | Hill | 260/665 G |
| 2,816,937 | 12/1957 | Ranosden | 260/665 G |
| 3,856,867 | 12/1974 | Ranosden | 260/665 G |
| 4,127,507 | 11/1978 | Fannin et al. | 260/665 G X |
| 5,093,046 | 3/1992 | Kober et al. | 260/665 G |

*Primary Examiner*—Paul F. Shaver
*Attorney, Agent, or Firm*—William E. Dickheiser

[57] ABSTRACT

Process for the preparation of compounds of formula (I):

$$Y-Mg-X \qquad (I)$$

wherein Y is an optionally substituted phenyl or benzyl, and X is a halogen, by reaction of a compound of formula (II):

$$Y-X \qquad (II)$$

wherein Y and X have the meanings given above, with magnesium in a solvent, characterized in that the solvent is an acetal of formula (III):

$$R^1-O-\underset{\underset{R^3}{|}}{CH}-O-R^2 \qquad (III)$$

wherein $R^1$ and $R^2$ are independently alkyl having from 1 to 6 carbon atoms or when taken together form a dioxolane ring, and $R^3$ is hydrogen or alkyl having from 1 to 6 carbon atoms.

10 Claims, No Drawings

CHEMICAL PROCESS

The present invention relates to a process for the preparation of aryl and aralkyl magnesium halides in acetal solvents.

The preparation of aryl and aralkyl magnesium halides in ethereal solutions is well know. The use of diethylether solvent is usual in Grignard reactions but the solvent has the significant hazard of a low flashpoint ($-40°$ C.) making it essential to carry out the process in specially modified process equipment. Construction of a commercial plant to carry out the process with diethylether necessarily involves high capital cost. Thus, the use of diethylether is hazardous to process operators and expensive in terms of the cost of process equipment. Other commonly used alternatives to diethylether such as tetrahydrofuran and glycoldimethylether result in large amounts of the dimer being produced during the reaction, particularly in the preparation of benzylmagnesium halides, unless high ratios of magnesium to starting material are used. This causes the process to be more expensive and provides the problem of disposing of the magnesium after the reaction.

EP 415 247 describes the use of tertiary-butylmethyl ether as an alternative solvent to the commonly used solvents in the Grignard reaction. Although this solvent has a flashpoint of $-28°$ C., this still represents a hazard and is apparently less effective than diethylether in terms of yield of product and suppression of dimerisation.

An alternative solvent with a higher flashpoint than diethylether and tertiary-butylmethyl ether has now been found which gives high yields of Grignard product and very low amounts of dimer when using nearly equimolar amounts of magnesium to starting material. The hazards associated with diethylether are avoided without any deleterious effect on the quality of the reaction.

Accordingly the present invention provides for a process for the preparation of compounds of formula (I):

$$Y-Mg-X \qquad (I)$$

wherein Y is an optionally substituted phenyl or benzyl, and X is a halogen, by reaction of a compound of formula (II):

$$Y-X \qquad (II)$$

wherein Y and X have the meanings given above, with magnesium in a solvent, characterised in that the solvent is an acetal of formula (III):

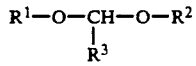
(III)

wherein $R^1$ and $R^2$ are independently alkyl having from 1 to 6 carbon atoms or when taken together form a dioxolane ring, and $R^3$ is hydrogen or alkyl having from 1 to 6 carbon atoms.

When Y is substituted, examples of suitable substituents for the phenyl and for the phenyl moiety of the benzyl are halogen, alkyl, alkoxy, haloalkyl, haloalkoxy, nitro, phenyl and phenoxy. The alkyl moiety of the benzyl can be substituted with alkyl, for example, methyl or ethyl.

When the phenyl group, or the phenyl moiety of the benzyl group is substituted with halogen, it is preferably substituted with fluorine, chlorine or bromine in one or more of the ortho, meta or para positions on the ring. Examples are 2-chlorophenyl, 3-chloro-phenyl, 4-chlorophenyl, 2,4-dichlorophenyl, 2,6-dichlorophenyl, 2-fluorophenyl, 3-fluorophenyl, 4-fluorophenyl, 2,4-difluorophenyl, 2,6-difluorophenyl, 2-chloro-4-fluorophenyl, 2-chloro-6-fluorophenyl, 2-chlorobenzyl, 3-chlorobenzyl, 4-chlorobenzyl, 2,4-dichlorobenzyl, 2,6-dichlorobenzyl, 2-fluorobenzyl, 3-fluorobenzyl, 4-fluorobenzyl, 2,4-difluorobenzyl, 2,6-difluorobenzyl.

Alternative substituents for the phenyl group, or the phenyl moiety of the benzyl group are $C_{1-8}$ alkyl, for example, methyl, ethyl, propyl (iso-or n-) or butyl (iso-, sec-, t-, or n-) in the ortho or para positions on the ring; $C_{1-6}$ haloalkyl, with fluorine or chlorine as the halogen, for example, trifluoromethyl, or pentafluoroethyl; $C_{1-6}$ alkoxy, for example, methoxy or ethoxy; $C_{1-6}$ haloalkoxy with fluorine or chlorine, for example, tetrafluoroethoxy.

The group X is preferably chlorine or bromine.

Preferred groups $R^1$, $R^2$ and $R^3$ for the solvent of formula (III) are methyl, ethyl, propyl and butyl. The alkyl groups are independent of each other and can be straight or branched chain, for example, isopropyl or tertiary-butyl. Of particular interest is diethoxymethane which has a flashpoint of $-6°$ C. (compared with a flashpoint of $-40°$ C. for diethylether).

The ratio of magnesium to starting material of formula (II) is preferably maintained in slight excess of the magnesium. A mole ratio of 1.01:1 to 20:1 is typical, particularly the ratios of 1.01:1 to 5:1 are recommended, especially 1.01:1 to 1.1:1.

The ratio of solvent to starting material is preferably from 2:1 to 30:1, especially 4:1 to 15:1.

The process is preferably performed at temperatures in the range of from $-10°$ to 100° C., especially from 0° to 60°·C. The process is normally conducted at atmospheric pressure and normally under inert gaseous conditions. Alternately the process can be carried out at the reflux temperature of the reaction mixture, for example, 80°-100° C.

EP 415 247 discloses the use of tertiary-butylmethyl ether as an alternative solvent to the commonly used solvents in the Grignard reaction.

Table I contains data published in EP 415 247 for diethylether and tertiary-butylmethyl ether for comparision with data from the examples given below for diethoxymethane and 2-methyl-1,3-dioxolane. The reactions were carried out using 2-chlorobenzylchloride as the starting material of formula (II).

TABLE I

| Solvent | Ratio of Mg:mol (II) | % conversion of (II) | % dimer-isation | % yield of Grignard |
|---|---|---|---|---|
| t-Butyl-O-Me | 1.2:1 | >95 | 10–15 | 75–80 |
| t-Butyl-O-Me | 6.0:1 | 95 | 0–5 | 85–90 |
| diethylether | 1.2:1 | 98.7 | <5 | 85–90 |

Table I shows that using the alternative solvent t-butylmethyl ehter, magnesium has to be maintained in significant excess in order to approach the level of yield of Grignard product and dimer by-product which is obtained when using diethylether. Clearly, the use of diethoxymethane, demonstrated in the Examples, gives conversion of starting material, yield of Grignard product and dimer by-product of the same order as with diethylether.

2-chlorobenzyl magnesium chloride from 2-chlorobenzyl chloride.

Further Examples were conducted using the method of Example 1. The results are presented in Table II.

TABLE II

| Example No. | Solvent | Solvent mols/mol halide | Magnesium mols/mol halide | Conversion of halide | % Yield of Grignard derivatives | % Dimer formation |
|---|---|---|---|---|---|---|
| 2 | diethoxymethane | 4.6 | 1.03 | 99.3 | 79.1 | 0.7 |
| 3 | diethoxymethane | 6.5 | 3.3 | 99.1 | 78.8 | 0.3 |
| 4 | 2-methyl-1,3-dioxolane | 4.6 | 1.03 | 99.4 | 79.0 | 0.6 |
| Comparative Examples | | | | | | |
| 5 | diethylether | 4.6 | 1.03 | 98.9 | 88.7 | 0.3 |
| 6 | diethylether | 6.5 | 3.3 | 99.5 | 92.0 | 0.3 |

Therefore, the acetal solvents disclosed herein, and in particular, diethoxymethane are excellent alternative solvents to etheral solvents normally used for forming the compounds of formula (I). The acetal solvents, particularly diethoxymethane, are surprisingly and unexpectedly at least as good as diethylether in giving high yield of Grignard product with low formation of dimer by-product, yet also have the advantage that the costs and hazards associated with using diethylether are avoided.

The invention is illustrated by the following Examples. Example 7 demonstrates the preparation of the epoxide via the formation of the compound of formula (I). The epoxide is an important intermediate in the preparation of fungicidal compounds, as disclosed in EP-A-15756. In the Examples the percentages are by weight and the following abbreviations are used: GLC=gas/liquid chromatography; NMR=nuclear magnetic resonance; d=doublet; m=multiplet; g=grammes; ml=milliliters; CDCl₃=deuterochloroform. Chemical shifts (d) are measured in parts per million from TMS and CDCl₃ or CCl₄ was used as solvent.

EXAMPLE 1

Preparation of 2-chlorobenzyl magnesium chloride using diethoxymethane as solvent Under a nitrogen atmosphere, 18.5 g of diethoxymethane and 3.05 g of magnesium were stirred together and 6.0 g of performed Grignard reagent solution was added, followed by 2.0 g of 2-chlorobenzyl chloride. A temperature rise of approximately 15° C. was noted. A further aliquot of diethoxymethane (57 g) was then added and the reaction cooled to 10°-15° C. A further aliquot of 2-chlorobenzyl chloride (17.5 g) was added over a period of 1 hour during which the temperature was maintained at 10°-15° C. After a further 1 hour, a GLC test showed virtual consumption of all the 2-chlorobenzyl chloride. The mole ratio of magnesium to 2-chlorobenzyl chloride was 1.05:1 and of solvent to 2-chlorobenzyl chloride was 6:1.

The Grignard reagent 2-chlorobenzyl magnesium chloride in diethoxymethane was quenched by cautious addition of a mixture of concentrated hydrochloric acid (14 g) and water (80 g). The aqueous phase was separated off and extracted twice with diethoxymethane. The organic layers were combined and the solvent removed on a rotary evaporator to give 17.5 g of a yellow oil containing 80% of 2-chlorotoluene and 1.7% of 2-chlorobenzyl alcohol, equivalent to 92.5% yield of

EXAMPLE 7

Preparation of 1,2-epoxy-2-(2-chlorobenzyl)-3,3-dimethyl butane using diethoxymethane as solvent

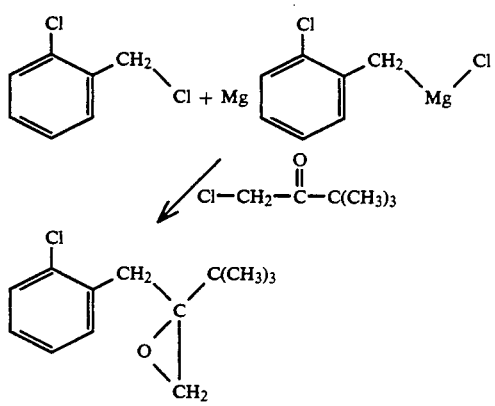

Under a nitrogen atmosphere, 70 ml of diethoxymethane and 3.1 g of magnesium were placed in a 250 ml round bottom flask fitted with a condenser and a stirrer. The reaction mixture was stirred at 17° C. in a water bath. Approximately 1 ml of preformed Grignard solution (methylmagnesium bromide) was added. No temperature rise was observed. 2-Chlorobenzyl chloride (20 g) was placed in a 100 ml pressure equalising dropping funnel and fitted to the reaction flask. Approximately 5% of the chlorobenzyl chloride was added. A temperature rise from 17° C. to 24° C. was observed and the reaction mixture was cooled to 10°-15° C. The remaining chlorobenzyl chloride was added over one hour maintaining the temperature at 10°-15° C.

The reaction mixture was then stirred for 2 hours at 10°-15° C. Monochloropinaclone (15.9 g) was added dropwise over 45 minutes at a temperature of 20°-25° C. The reaction mixture was stirred for one hour then drowned into ammonium chloride solution and extracted twice with diethoxymethane. The diethoxymethane extracts were combined, dried over anhydrous sodium sulphate, filtered and evaporated to give a yellow oil (26.9 g at 78.8% strength by GLC). The title epoxide was identified by GLC comparison with an authentic sample (NMR given below).

Yield of epoxide=80.0%.

% of dimer present after reaction=1.8%.
1H NMR δ (CDCl3): 7.05-7.4 (m, 4H) aromatic, 3.01-3.38 (d, 2H), 1.01-1.16 (m, 9H), 1.82-2.54 (d, 2H).

EXAMPLE 8

Comparative

Preparation of 1,2-epoxy-2-(2-chlorobenzyl)-3,3-dimethyl butane using diethylether as solvent Under a nitrogen atmosphere, 60 ml of diethylether and 3.1 g of magnesium were placed in a 250 ml round bottom flask fitted with a stirrer, a thermometer and a dry ice condenser. The mixture was stirred at room temperature and 2.0 ml of preformed Grignard solution (methylmagnesium bromide) was added. A temperature rise of approximately 5° C. was observed. 2-Chlorobenzyl chloride (20.0 g) was placed in a 100 ml pressure equalising dropping funnel and fitted to the reaction flask which was cooled to 10° C. Approximately 10% of the 2-chlorobenzyl chloride was added to initiate the reaction. After initiation had taken place the remainder of the 2-chlorobenzyl chloride was added over approximately 1½ hours maintaining the temperature at 10°-15° C. with an ice/water bath.

The reaction mixture was stirred for 1 hour then monochloropinacolone (15.9 g) was placed in a dropping funnel and added dropwise at 20°-25° C. The reaction mixture was drowned out into aqueous ammonium chloride and the product extracted into diethylether. The ether extracts were combined, dried over anhydrous sodium sulphate, filtered and evaporated to give a cloudy yellow oil (26.8 g at 79.6% strength by GLC). The title epoxide was identified by GLC comparision with the authentic sample.

Yield of epoxide=80.4%.
% of dimer present after reaction=1.6%.

We claim:

1. A process for the preparation of compounds of formula (I):

$$Y-Mg-X \qquad (I)$$

wherein Y is an unsubstituted or substituted phenyl or benzyl, and X is a halogen, by reaction of a compound of formula (II):

$$Y-X \qquad (II)$$

wherein Y and X have the meanings given above, with magnesium in a solvent, characterised in that the solvent is an acetal of formula (III):

$$R^1-O-\underset{\underset{R^3}{|}}{CH}-O-R^2 \qquad (III)$$

wherein $R^1$ and $R^2$ are independently alkyl having from 1 to 6 carbon atoms or when taken together form a dioxolane ring, and $R^3$ is hydrogen or alkyl having from 1 to 6 carbon atoms.

2. A process according to claim 1 wherein the phenyl or the phenyl moiety of the benzyl of Y is unsubstituted or substituted with one or more substitutents selected from halogen, alkyl, alkoxy, haloalkyl, haloalkoxy, nitro, phenyl and phenoxy.

3. A process according to claim 2 wherein the phenyl or the phenyl moiety of the benzyl of Y is unsubstituted or substituted with one or more substitutents selected from chlorine, fluorine, $C_{1-8}$ alkyl, $C_{1-6}$ alkoxy, $C_{1-6}$ haloalkoxy, nitro, phenyl and phenoxy.

4. A process according to claim 1 wherein Y is unsubstituted or substituted benzyl.

5. A process according to claim 4 wherein Y is 2-chlorobenzyl.

6. A process according to claim 1 wherein $R^1$ and $R^2$ are independently methyl, ethyl, propyl or butyl.

7. A process according to claim 1 wherein $R^3$ is methyl, ethyl, propyl or butyl.

8. A process according to claim 1 wherein the solvent of formula (III) is diethoxymethane.

9. A process according to claim 1 wherein the solvent of formula (III) is 2-methyl-1,3-dioxolane.

10. A process according to claim 1 wherein the quantity of magnesium is from 1.01 to 20 mole per mole of starting material of formula (II).

* * * * *